United States Patent [19]

Sasajima et al.

[11] 4,075,346
[45] Feb. 21, 1978

[54] CNS DEPRESSANT γ-(SECONDARY AMINO)-ORTHO-NITRO-BUTYROPHE-NONES

[75] Inventors: Kikuo Sasajima, Toyonaka; Keiichi Ono, Nishinomiya; Yasuo Motoike, Minoo; Shigeho Inaba, Takarazuka; Hisao Yamamoto, Kobe, all of Japan

[73] Assignee: Sumitomo Chemical Company, Limited, Japan

[21] Appl. No.: 705,840

[22] Filed: July 16, 1976

[30] Foreign Application Priority Data

July 17, 1975 Japan ............................ 50-87962
July 18, 1975 Japan ............................ 50-88473

[51] Int. Cl.² ............... C07D 211/28; A61K 31/445
[52] U.S. Cl. .................. 424/267; 260/268 PH;
260/293.6; 260/293.66; 260/293.67;
260/293.68; 260/293.79; 260/293.8; 260/343.6;
260/592; 424/250
[58] Field of Search ........... 260/293.8, 293.67, 293.68;
424/267

[56] References Cited
U.S. PATENT DOCUMENTS 3,408,356 10/1968 Horovitz ........................... 260/294.3
3,799,932 3/1974 Yamamoto et al. .............. 260/293.6

Primary Examiner—Cecilia M. S. Jaisle
Attorney, Agent, or Firm—Birch, Stewart, Kolasch and Birch

[57] ABSTRACT

Novel compounds of the formula:

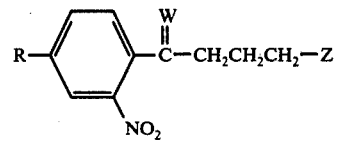

wherein R is a hydrogen or fluorine atom, W is an oxygen atom or an ethylenedioxy or ethylenedithio group and Z is a certain secondary amino group, which are useful as central nervous system depressants, can be prepared by the reaction of a compound of the formula:

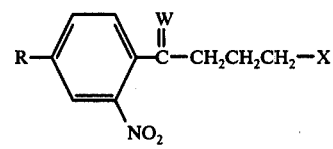

wherein X is a halogen atom and R and W are each as defined above with a secondary amine of the formula: H—Z wherein Z is as defined above, in case of W being ethylenedioxy or ethylenedithio, optionally followed by hydrolysis and can be reduced to give a compound of the formula:

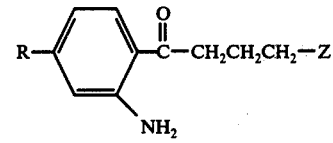

wherein R and Z are each as defined above, which are useful as antipsychotic and/or analgesic agents.

8 Claims, No Drawings

CNS DEPRESSANT γ-(SECONDARY AMINO)-ORTHO-NITRO-BUTYROPHENONES

This invention relates to an improved process for producing ortho-aminobutyrophenone derivatives and their salts, which are known to be useful as antipsychotic and/or analgesic agents, and to novel ortho-nitrobutyrophenone derivatives and their salts, which are intermediates in the said process and per se useful as central nervous system depressants.

The said ortho-aminobutyrophenone derivatives are representable by the formula:

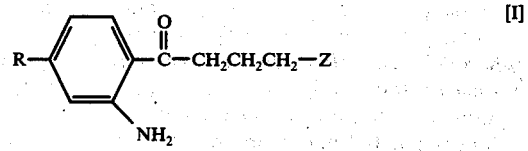

wherein R is a hydrogen atom or a fluorine atom and Z is a secondary amino group of either one of the formulas:

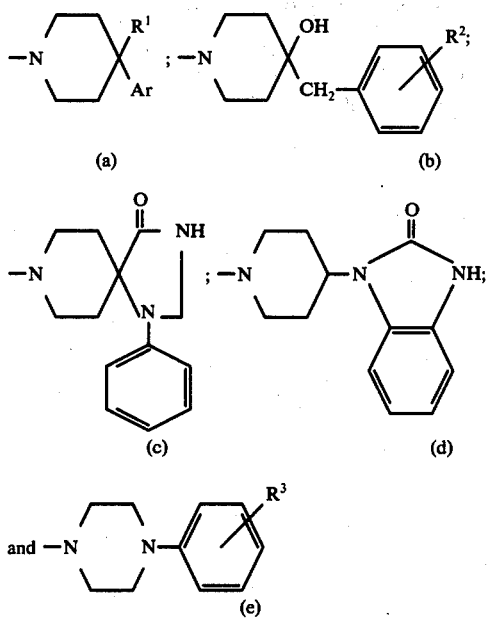

(wherein Ar is a phenyl group optionally substituted with one or two substituents selected from the group consisting of halogen (e.g. chlorine, bromine, fluorine), methyl, methoxy and trifluoromethyl, $R^1$ is a hydrogen atom or a hydroxyl group, $R^2$ is a hydrogen atom or a halogen atom (e.g. chlorine, bromine, fluorine) and $R^3$ is a hydrogen atom or a methoxy group).

The said ortho-nitrobutyrophenone derivatives include γ-(secondary amino)-ortho-nitrobutyrophenones of the formula:

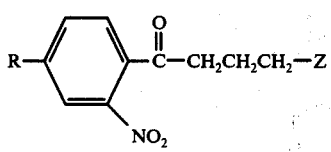

wherein R and Z are each as defined above and their ketals of the formula:

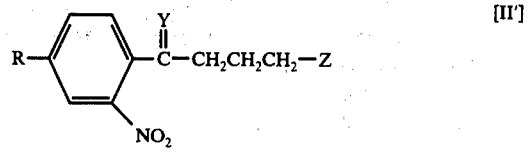

wherein Y is an ethylenedioxy group or an ethylenedithio group and R and Z are each as defined above.

The γ-(secondary amino)-ortho-aminobutyrophenones [I] and the methods for producing them are well known in the literature [cf. Belgian Pat. Nos. 753,472 and 796,893].

Investigations were made extensively in order to find an advantageous process for preparing the γ-(secondary amino)-ortho-aminobutyrophenones [I]. As the result, a novel and commercially advantageous process has now been established.

According to the present invention, the γ-(secondary amino)-ortho-aminobutyrophenone [I] can be prepared from the corresponding γ-(secondary amino)-ortho-nitrobutyrophenone [II] or its ketal [II'] by reduction of the latter, in case of the ketal, with previous or subsequent hydrolysis.

The γ-(secondary amino)-ortho-nitrobutyrophenone [II] and its ketal [II'] are novel and can be advantageously prepared by reacting the corresponding γ-(halo)-ortho-nitrobutyrophenone of the formula:

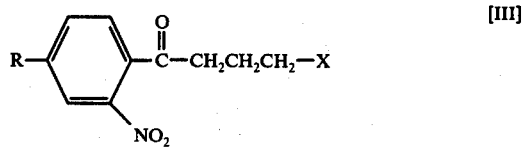

wherein X is a halogen atom (e.g. chlorine, bromine) and R is as defined above or its ketal with a secondary amine of the formula:

H—Z wherein Z is as defined above, in case of the ketal, optionally followed by hydrolysis.

The γ-(halo)-ortho-nitrobutyrophenone [III] and its ketal, which are also novel, can be produced advantageously by reacting an ortho-nitrobenzoic acid derivative of the formula:

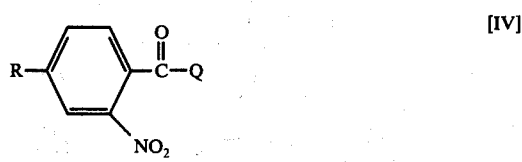

wherein Q is a halogen atom (e.g. chlorine, bromine) or a group of the formula:

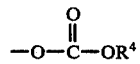

(wherein $R^4$ is a $C_1-C_3$ alkyl group (e.g. methyl, ethyl, propyl)) and R is as defined above with an α-(alkanoyl)-γ-butyrolactone of the formula:

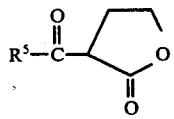
[V]

wherein $R^5$ is a $C_1-C_3$ alkyl group (e.g. methyl, ethyl, propyl) to give the corresponding α-(ortho-nitrobenzoyl)-γ-butyrolactone derivative of the formula:

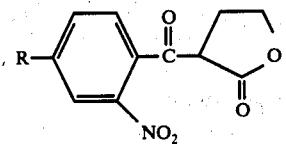
[VI]

wherein R is as defined above and/or the corresponding α-(alkanoyl)-α-(ortho-nitrobenzoyl)-γ-butyrolactone derivative of the formula:

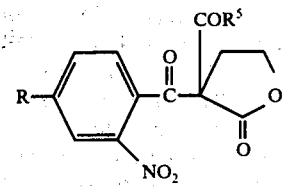
[VII]

wherein R and $R^5$ are each as defined above and, in case of the α,α-(diacyl)-γ-butyrolactone [VII] being produced, deacylating the same to the corresponding α-(acyl)-γ-butyrolactone [VI], followed by reaction with a hydrohalogenic acid of the formula:

H—X wherein X is as defined above to give the corresponding γ-(halo)-ortho-nitrobutyrophenone [III], which may be optionally ketalized to give the corresponding ketal.

The sequential steps from the ortho-nitrobenzoic acid derivative [IV] and the α-(alkanoyl)-γ-butyrolactone [V] through the γ-(halo)-ortho-nitrobutyrophenone [III] or its ketal and the γ-(secondary amino)-ortho-nitrobutyrophenone [II] or its ketal to the γ-(secondary amino)-orthoaminobutyrophenone [I] as stated above are representable by the following schema:

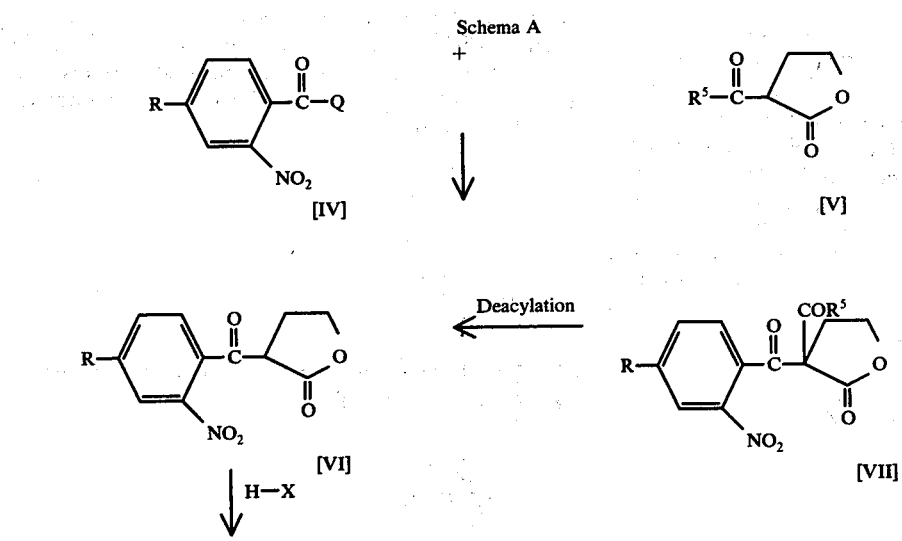

Schema A

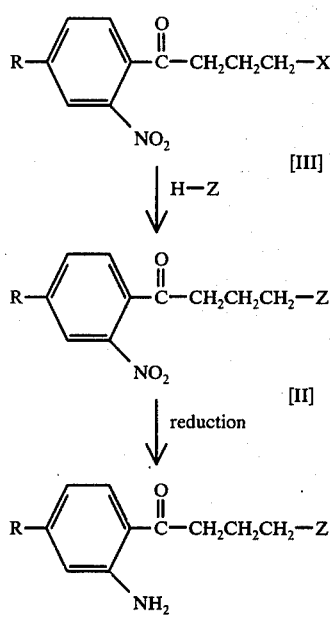

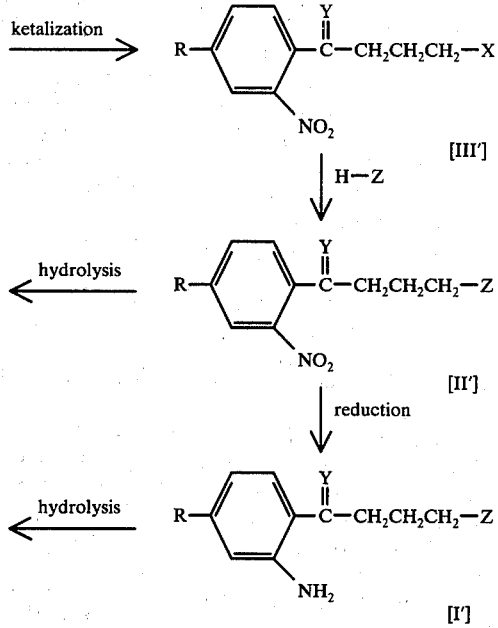

wherein R, X, Y, Z, $R^5$ and Q are each as defined above.

In the above schema, the conversion in the latter two stages can be summarized by the following formulas:

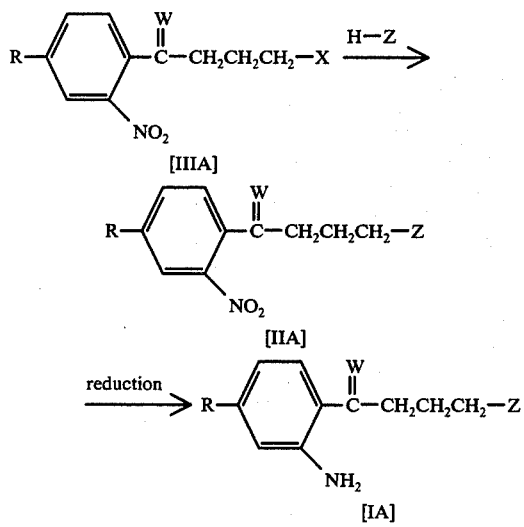

wherein W is an oxygen atom, an ethylenedioxy group or an ethylenedithio group and R, X and Z are each as defined above.

The production of γ-(halo)-ortho-nitrobutyrophenone derivatives by nitration of the corresponding γ-(halo)-butyrophenone derivatives, of which the conversion is representable by the following formulas, is known [cf. U.S. Pat. No. 3,562,277]:

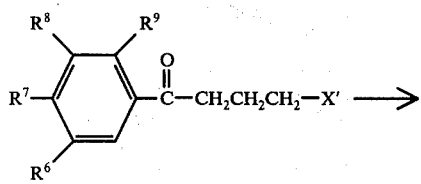

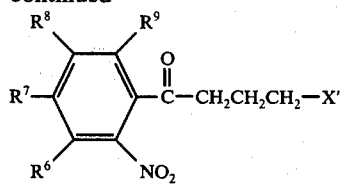

wherein X' is a halogen atom and $R^6$ to $R^9$ are each a hydrogen atom or a lower alkoxy group, at least one of $R^6$ to $R^9$ being a hydrogen atom, or any two adjacent members of $R^6$ to $R_9$ taken together form a methylenedioxy group. Adoption of such nitration in the production of the γ-(halo)-ortho-nitrobutyrophenone [III], however, is apparently disadvantageous, because the main nitration product is the undesired meta-nitrated compound [cf. British Pat. No. 943,739].

In the present invention, an entirely different route is recommended to produce the γ-(halo)-ortho-nitrobutyrophenone [III] in a good yield. Thus, it may be produced from the ortho-nitrobenzoic acid derivative [IV] and the α-(alkanoyl)-γ-butyrolactone [V] through the α-(ortho-nitrobenzoyl)-γ-butyrolactone [VI] at stated above.

The process of the present invention will be illustrated below in details according to the sequence of the reaction steps.

Step 1

Production of the α-(ortho-nitrobenzoyl)-γ-butyrolactone [VI]:

The reaction of the ortho-nitrobenzoic acid derivative [IV] with the α-(alkanoyl)-γ-butyrolactone [V] is usually carried out in the presence of a base in an inert solvent. As the base, there may be used an alkali metal or alkaline earth metal alkoxide (e.g. sodium alkoxide, potassium alkoxide, magnesium alkoxide), an alkali metal hydride (e.g. sodium hydride, potassium hydride, lithium hydride), an alkali metal amide (e.g. sodium amide, potassium amide, lithium dialkylamide), an alkali metal salt of triphenylmethane, an organic lithium compound (e.g. n-butyl lithium, phenyl lithium), an alkali metal methylsulfinyl carbanion, etc. Examples of the inert solvent include ethers (e.g. diethyl ether, 1,2-dimethoxyethane, tetrahydrofuran), aromatic hydrocarbons (e.g. benzene, toluene) and aprotic polar solvents (e.g. dimethylformamide, dimethyl sulfoxide, hexamethylene phosphoramide). Although various combinations of the base and the solvent may be employed in this reaction, it is preferable to use a magnesium alkoxide (e.g. magnesium methoxide, magnesium ethoxide) or an alkali metal hydride (e.g. sodium hydride) in an inert solvent such as an ether and an aromatic hydrocarbon.

Among the ortho-nitrobenzoic acid derivative [IV], the use of the one wherein Q is chlorine, bromine or ethoxycarbonyloxy is preferred. As the α-(alkanoyl)-γ-butyrolactone [V], the use of α-acetyl-γ-butyrolactone is favorable, since it is commercially available.

For the practical procedure of the reaction, the α-(alkanoyl)-γ-butyrolactone [V] may be first treated with the base to form the carbanion or enol anion, which is then subjected to treatment with the ortho-nitrobenzoic acid derivative [IV]. The proportion of the ortho-nitrobenzoic acid derivative [IV] and the α-(alkanoyl)-γ-butyrolactone [V] may be usually 0.2-2:1 in molar ratio. The amount of the base to be used can be decided appropriately depending in its kind. When, for instance, magnesium alkoxide is used as the base, the molar ratio of the α-(alkanoyl)-γ-butyrolactone [V] to the base may be from 1 to 3.

As the result of the reaction, there are produced the α-(acyl)-γ-butyrolactone [VI] and/or the α,α-(diacyl)-γ-butyrolactone [VII]. By adoption of suitable reaction and/or isolation conditions, there is obtainable predominantly or solely either one of them. When the α,α-(diacyl)-γ-butyrolactone [VII] is obtained as the main product, it may be converted into the corresponding α-(acyl)-γ-butyrolactone [VI] by deacylation. The deacylation can be accomplished by treatment with an alkali such as ammonia, an alkali metal hydroxide, an alkali metal carbonate or an alkali metal bicarbonate in a suitable solvent such as water or an alkanol. For instance, the α, α-(diacyl)-γ-butyrolactone [VII] may be shaken with a dilute aqueous ammonium hydroxide solution in the presence of a water-immiscible organic solvent at room temperature for a few minutes to give the corresponding α-(acyl)-γ-butyrolactone [VI].

Specific examples of the α-(acyl)-γ-butyrolactone [VI] are α-(4-fluoro-2-nitrobenzoyl)-γ-butyrolactone and α-(2-nitrobenzoyl)-γ-butyrolactone.

Step 2

Production of the γ-(halo)-ortho-nitrobutyrophenone [III] and its ketal [III']:

The α-(acyl)-γ-butyrolactone [VI] can be readily converted into the corresponding γ-(halo)-ortho-nitrobutyrophenone [III] by reacting with a hydrohalogenic acid (e.g. hydrochloric acid, hydrobromic acid, hydroiodic acid). The reaction is usually carried out by keeping a mixture of the α-(acyl)-γ-butyrolactone [VI] and the hydrohalogenic acid, optionally in an inert solvent such as an ether, an aromatic hydrocarbon or a ketone at an elevated temperature above room temperature, particularly above 50° C. While the hydrohalogenic acid may be employed in a not less than equimolar amount to the α-(acyl)-γ-butyrolactone [VI], the use in a larger amount such as three or more equivalents can accelerate the progress of the reaction.

The thus produced γ-(halo)-ortho-nitrobutyrophenone [III] may be recovered from the reaction mixture by a conventional separation procedure, for instance, extraction with a suitable solvent and concentration of the extract.

Conversion of the γ-(halo)-ortho-nitrobutyrophenone [III] into its ketal [III'] may be carried out in a per se conventional ketalization procedure, for instance, by treatment with ethylene glycol or ethylene dithioglycol in the presence of an acid catalyst such as p-toluenesulfonic acid, sulfuric acid, hydrogen chloride or a Lewis acid (e.g. boron trifluoride, stannic chloride) in a suitable inert solvent. The water by-produced in the reaction may be eliminated from the reaction system by various procedures, of which examples are azeotropic distillation with a water-immiscible organic solvent, slow distillation in vacuo, treatment with a Lewis acid catalyst, treatment with a scavenger such as an ortho ester (e.g. ethyl ortho-formate), ethylene sulfite or molecular sieves.

Specific examples of the γ-(halo)-ortho-nitrobutyrophenone [III] and its ketal [III'] are γ-chloro-4-fluoro-2-nitrobutyrophenone, γ-bromo-4fluoro-2-nitrobutyrophenone, γ-iodo-4-fluoro-2-nitrobutyrophenone, γ-chloro-2-nitrobutyrophenone, γ-bromo-2nitrobutyrophenone, γ-iodo-2-nitrobutyrophenone, 4-chloro-1-(4-fluoro-2-nitrophenyl)-1,1-ethylenedioxy-n-butane, 4-bromo-1-(4-fluoro-2-nitrophenyl)-1,1-ethylenedioxy-n-butane, 4-chloro-1-(2-nitrophenyl)-1,1-ethylenedioxy-n-butane, 4-bromo-1-(2-nitrophenyl)-1,1-ethylenedioxy-n-butane.

Step 3

Production of the γ-(secondary amino)-ortho -nitrobutyrophenone [II] and its ketal [II']:

The γ-(halo)-ortho-nitrobutyrophenone [III] and its ketal [III'] can be respectively converted into the corresponding γ-(secondary amino)-ortho-nitrobutyrophenone [II] and its ketal [II'] by reaction of the former with the secondary amine (H—Z). The reaction may be effected in the presence of an acid binding agent such as an inorganic base (e.g. potassium carbonate, sodium carbonate, sodium bicarbonate) or a tertiary amine (e.g. pyridine, triethylamine, dimethylaniline) in the presence or absence of a suitable solvent. Examples of the suitable solvent are an amide (e.g. dimethylformamide, dimethylacetamide, formamide), an aromatic hydrocarbon (e.g. benzene, toluene, xylene), an alkanone (e.g. acetone, methyl ethyl ketone, methyl isobutyl ketone), an ether (e.g. tetrahydrofuran, dioxane), an alkanol (e.g. ethanol, propanol, butanol), etc. The reaction can be conducted at a wide range of temperature from room temperature to the refluxing temperature of the reaction system, and a higher temperature is generally preferred. When, however, the ketal [II'] is subjected to the reaction, somewhat a milder condition, for example, a temperature below 90° C is favorable.

Hydrolysis of the ketal [II'] into the γ-(secondary amino)-ortho-nitrobutyrophenone [II] may be accomplished by a per se conventional procedure. For example, it can be conducted by treatment with a mineral acid (e.g. hydrochloric acid, sulfuric acid, phosphoric acid), an organic acid (e.g. oxalic acid, tartaric acid) or an acidic ion exchange resin in water or an alkanol (e.g. methanol, ethanol, propanol). The cleavage of the ketal group can be also effected by exchange with acetone in the presence of a mineral acid, and such cleavage is facilitated in the presence of periodic acid.

Specific examples of the γ-(secondary amino)-ortho-nitrobutyrophenone [II] and its ketal [II'] are as follows:

γ-[4-Hydroxy-4-(3-trifluoromethylphenyl)-piperidino]-4-fluoro-2-nitrobutyrophenone;

γ-[4-(4-Chlorophenyl)-4-hydroxypiperidino]-4-fluoro-2-nitrobutyrophenone;

γ-[4-(4-Chloro-3-trifluoromethylphenyl)-4-hydroxypiperidino]-4-fluoro-2-nitrobutyrophenone;

γ-[4-(3,4-Dichlorophenyl)-4-hydroxypiperidino]-4-fluoro-2-nitrobutyrophenone;

γ-[4-(3-Chloro-4-methylphenyl)-4-hydroxypiperidino]-4-fluoro-2-nitrobutyrophenone;

γ-(4-Phenylpiperidino)-4-fluoro-2-nitrobutyrophenone;

γ-(4-Oxo-1-phenyl-1,3,8-triazaspiro[4,5]decan-8-yl)-4-fluoro-2-nitrobutyrophenone;

γ-[4-(2-Oxo-1-benzimidazolinyl)piperidino]-4-fluoro-2-nitrobutyrophenone;

γ-[4-(4-Chlorobenzyl)-4-hydroxypiperidino]-4-fluoro-2-nitrobutyrophenone;

γ-[4-(2-Methoxyphenyl)piperazino]-4-fluoro-2-nitrobutyrophenone;

γ-[4-Hydroxy-4-(4-methylphenyl)piperidino]-4-fluoro-2-nitrobutyrophenone;

γ-[4-Hydroxy-4-(4-methoxyphenyl)piperidino]-4-fluoro-2-nitrobutyrophenone;

γ-[4-Hydroxy-4-(3-trifluoromethylphenyl)-piperidino]-2-nitrobutyrophenone;

γ-[4-(4-Chlorophenyl)-4-hydroxypiperidino]-2-nitrobutyrophenone;

γ-(4-Benzyl-4-hydroxypiperidino)-2-nitrobutyrophenone;

γ-[4-(4-Chlorobenzyl)-4-hydroxypiperidino]-2-nitrobutyrophenone;

γ-[4-(4-Chloro-3-trifluoromethylphenyl)-4-hydroxypiperidino]-2-nitrobutyrophenone;

γ-(4-Oxo-1-phenyl-1,3,8-triazaspiro[4,5]decan-8-yl)-2-nitrobutyrophenone;

γ-[4-(2-Oxo-1-benzimidazolinyl)piperidino]-2-nitrobutyrophenone;

γ-[4-(2-Methoxyphenyl)piperazino]-2-nitrobutyrophenone;

4-[4-Hydroxy-4-(3-trifluoromethylphenyl)-piperidino]-1-(4-fluoro-2-nitrophenyl)-1,1-ethylenedioxy-n-butane;

4-[4-(4-Chlorophenyl)-4-hydroxypiperidino]-1-(4-fluoro-2-nitrophenyl)-1,1-ethylenedioxy-n-butane;

4-[4-(4-Chloro-3-trifluoromethylphenyl)-4-hydroxypiperidino]-1-(4-fluoro-2-nitrophenyl)-1,1-ethylenedioxy-n-butane;

4-(4-Oxo-1-phenyl-1,3,8-triazaspiro[4,5]decan-8-yl)-1-(4-fluoro-2-nitrophenyl)-1,1-ethylenedioxy-n-butane;

4-[4-(2-Oxo-1-benzimidazolinyl)piperidino]-1-(4-fluoro-2-nitrophenyl)-1,1-ethylenedioxy-n-butane.

The thus prepared γ-(secondary amino)-ortho-nitrobutyrophenone [II] or its ketal [II'] can be readily converted into its inorganic or organic acid addition salts by a per se conventional procedure. Examples of such salts include pharmaceutically acceptable ones such as the hydrochloride, hydrobromide, sulfate, phosphate, sulfamate, citrate, oxalate, lactate, maleate, malate, succinate, tartrate, cinnamate, acetate, benzoate, gluconate, ascorbate, fumarate, glutamate, salicylate and the like.

The γ-(secondary-amino)-ortho-nitrobutyrophenone [II] and its ketal [II'] and their acid addition salts thus obtained have useful central nervous system depressive activities. Some ortho-nitrobutyrophenone compounds similar thereto are disclosed in U.S. Pat. No. 3,562,277, but in the specification of this patent, it is stated that those γ-(piperazino)-ortho-nitrobutyrophenones have less central nervous system activity. The γ-(secondary amino)-ortho-nitrobutyrophenone [II] and its ketal [II'] and their acid addition salts of the present invention have been found to exert various central nervous system depressive activities in the standard screening tests in animals and are useful as medicaments such as antipsychotics, sedatives, tranquilizers and analgesics. The γ-(secondary amino)-ortho-nitro-parafluorobutyrophenone [II: R = fluorine] and its acid addition salts are the most preferable compounds as antipsychotics and are superior to Chlorpromazine. These compounds of this invention are useful in causing depression of the central nervous system of mammals in a daily dose of about 0.5 to 300 mg per os.

Step 4

Production of the γ-(secondary amino)-ortho-aminobutyrophenone [I] and its ketal [I'] :

Reduction of the γ-(secondary amino)-ortho-nitrobutyrophenone [II] and its ketal [II'] afford respectively the γ-(secondary amino)-ortho-aminobutyrophenone [I] and its ketal [I']. The γ-(secondary amino)-ortho-nitrobutyrophenone [II] or its ketal [II'] may be subjected to the reduction in the form of a free base or an acid addition salt.

Although various reducing agents and systems which have heretofore been adopted for conversion of a nitro group into an amino group such as treatment with a metal or its salt in the presence of an acid or an alkali, treatment with an alkali sulfide or polysulfide in the presence of an alkali or catalytic hydrogenation are applicable for accomplishment of the reduction in this step, preferable are treatment with a metal (e.g. iron, tin, zinc) or its salt (e.g. stannous chloride) in the presence of an acid (e.g. hydrochloric acid, sulfuric acid, acetic acid) or catalytic hydrogenation using as the catalyst palladium on charcoal, nickel or the like.

Preferably, the reduction is carried out in the presence of an inert solvent such as water, an alkanol (e.g. methanol, ethanol, propanol), an aromatic hydrocarbon (e.g. benzene, toluene), an alkanone (e.g. acetone, methyl ethyl ketone) or an ether (e.g. tetrahydrofuran, dioxane). The hydrogenation is preferably conducted in the presence of palladium on charcoal in a $C_1$–$C_3$ alkanol and, in most cases, proceeds readily at room temperature under atmospheric pressure of hydrogen.

In case of the ketal [II'] being subjected to the reduction, there are produced the γ-(secondary amino)-ortho-aminobutyrophenone [I] and/or its ketal [I'] depending on the reaction conditions. When the ketal [I'] is produced, it can be converted into the corresponding γ-(secondary amino)-ortho-aminobutyrophenone [I] by hydrolysis in the substantially same manner as described in Step 3.

Recovery of the γ-(secondary amino)-ortho-aminobutyrophenone [I] and/or its ketal [I'] from the reaction mixture may be achieved by application of a conventional procedure for separation and purification.

Specific examples of the γ-(secondary amino)-ortho-aminobutyrophenone [I] and its ketal [I'] are as follows:

γ-[4-Hydroxy-4-(3-trifluoromethylphenyl)-piperidino]-2-amino-4-fluorobutyrophenone;

γ-[4-(4-Chlorophenyl)-4-hydroxypiperidino]-2-amino-4-fluorobutyrophenone;

γ-[4-(4-Chloro-3-trifluoromethylphenyl)-4-hydroxypiperidino]-2-amino-4-fluorobutyrophenone;

γ-[4-(3,4-Dichlorophenyl)-4-hydroxypiperidino]-2-amino-4-fluorobutyrophenone;

γ-[4-(3-Chloro-4-methylphenyl)piperidino]-2-amino-4-fluorobutyrophenone;

γ-(4-Phenylpiperidino)-2-amino-4-fluorobutyrophenone;

γ-(4-Oxo-1-phenyl-1,3,8-triazaspiro[4,5]decan-8-yl)-2-amino-4-fluorobutyrophenone;

γ-[4-(2-Oxo-1-benzimidazolinyl)piperidino]-2-amino-4-fluorobutyrophenone;

γ-[4-(4-Chlorobenzyl)-4-hydroxypiperidino]-2-amino-4-fluorobutyrophenone;

γ-[4-(2-Methoxyphenyl)piperazino]-2-amino-4-fluorobutyrophenone;

γ-[4-Hydroxy-4-(4-methylphenyl)piperidino]-2-amino-4-fluorobutyrophenone;

γ-(4-Benzyl-4-hydroxypiperidino)-2-aminobutyrophenone;

γ-[4-(4-Chlorobenzyl)-4-hydroxypiperidino]-2-aminobutyrophenone;

γ-(4-Oxo-1-phenyl-1,3,8-triazaspiro[4,5]decan-8-yl)-2-aminobutyrophenone;

4-[4-Hydroxy-4-(3-trifluoromethylphenyl)piperidino]-1-(2-amino-4-fluorophenyl)-1,1-ethylenedioxy-n-butane;

4-[4-(3,4-Dichlorophenyl)-4-hydroxypiperidino]-1-(2-amino-4-fluorophenyl)-1,1-ethylenedioxy-n-butane;

4-[4-(3-Chloro-4-methylphenyl)-4-hydroxypiperidino]-1-(2-amino-4-fluorophenyl)-1,1-ethylenedioxy-n-butane;

4-(4-Oxo-1-phenyl-1,3,8-triazaspiro[4,5]decan-8-yl)-1-(2-amino-4-fluorophenyl)-1,1-ethylenedioxy-n-butane;

4-[4-(2-Oxo-1-benzimidazolinyl)piperidino]-1-(2-amino-4-fluorophenyl)-1,1-ethylenedioxy-n-butane.

The thus prepared γ-(secondary amino)-ortho-aminobutyrophenone [I] or its ketal [I'] can be readily converted into its inorganic or organic acid addition salts as exemplified in Step 3 by a conventional procedure.

As stated above, the γ-(secondary amino)-ortho-aminobutyrophenone [I] and its acid addition salts are known to be useful as antipsychotic and/or analgesic agents.

Practical and presently preferred embodiments of the invention are illustratively shown in the following examples without limiting the scope of the invention in any way.

EXAMPLE 1

(A) A mixture of 8.0 g of magnesium turnings, 33 g of anhydrous ethanol and 3 ml of carbon tetrachloride was allowed to react on standing for several minutes. After the exothermic reaction had subsided, 250 ml of anhydrous toluene was slowly added under stirring, and the reaction mixture was stirred at 30°–35° C for an additional 3 hours. To the resulting suspension of magnesium ethoxide, a solution of 84.6 g of α-acetyl-γ-butyrolactone in 100 ml of anhydrous toluene was added dropwise under cooling at 0°–5° C. After the resulting mixture was stirred at room temperature for one hour, crude 4-fluoro-2-nitrobenzoyl chloride, prepared from 55.5 g of 4-fluoro-2-nitrobenzoic acid and 170 ml of thionyl chloride, in 100 ml of anhydrous toluene was added dropwise at 20°–25° C and stirred for an additional 3 hours. After 700 ml of 5% sulfuric acid was added to the resulting mixture under cooling with an ice-salt bath, the organic layer was separated, and the aqueous layer was extracted with portions of toluene. The resulting organic layer contained α-acetyl-α-(4-fluoro-2-nitrobenzoyl)-γ-butyrolactone as the main product. The combined organic layer was washed with water and aqueous saturated sodium chloride solution and extracted with three portions of cold 5% aqueous ammonium hydroxide solution. The combined aqueous ammonium hydroxide layer was washed with toluene and acidified by slow addition of 25% sulfuric acid under cooling. The precipitated solid was collected by filtration, washed with water and dried to give 63.5 g (83.6%) of α-(4-fluoro-2-nitrobenzoyl)-γ-butyrolactone. M.P. 87°–89° C.

(B) Using an equimolar amount of magnesium ethoxide instead of the one prepared from magnesium in ethanol in (A), the same product was also obtained in a yield of 79.3%. M.P. 86.5°–89.0° C.

(C) A mixture of 16.2 g of magnesium turnings, 67.5 g of anhydrous ethanol and 5 ml of carbon tetrachloride was allowed to react on standing for several minutes. After the exothermic reaction had subsided, 500 ml of anhydrous toluene was slowly added under stirring, and the resulting mixture was stirred at 35°–40° C for an additional 2 hours. To the resulting mixture, a solution of α-acetyl-γ-butyro lactone (170.8 g) in anhydrous toluene (200 ml) was added thereto dropwise under cooling below 10° C, and the resultant mixture was stirred at room temperature for 1 hour. A solution of o-nitrobenzoyl chloride, prepared from 100 g of the corresponding acid, in anhydrous toluene (200 ml) was added thereto dropwise at 20°–25° C, and stirring was carried out for an additional 2 hours. Under cooling, 1.4 liters of 5% sulfuric acid was slowly added to the resulting mixture, and the whole was extracted with ethyl acetate (900 ml). The aqueous layer was extracted with two portions of toluene-ethyl acetate (1:1), and the combined extracts were washed with water and aqueous saturated sodium chloride solution and extracted with three portions of cold 5% aqueous ammonium hydroxide solution (840 g × 3). The combined aqueous layer was washed with toluene and acidified with 25% sulfuric acid under cooling. The precipitated crystals were collected by filtration, washed with water and dried to give 120 g (85%) of α-(2-nitrobenzoyl)-γ-butyrolactone. M.P. 75°–76° C.

EXAMPLE 2

(A) A mixture of 20.0 g of α-(4-fluoro-2-nitrobenzoyl)-γ-butyrolactone and 66.6 g of hydrobromic acid (d = 1.48) was warmed at 85° C until the evolution of carbon dioxide ceased. After warming for an additional 30 minutes, the reaction mixture was diluted with 300 ml of cold water and extracted with toluene. The extracts were washed with water, dried over anhydrous sodium sulfate and concentrated under reduced pressure to yield 21.7 g (95%) of γ-bromo-4-fluoro-2-nitrobutyrophenone as an oil. B.P. 139°–148° C (at 0.18–0.20 mmHg).

(B) A mixture of 5.06 g of α-(4-fluoro-2-nitrobenzoyl)-γ-butyrolactone and 20 ml of concentrated hydrochloric acid was treated as in (A) to give 4.4 g (90%) of γ-chloro-4-fluoro-2-nitrobutyrophenone. B.P. 132.0°–132.5° C (at 0.17–0.19 mmHg).

(C) In the same manner as above, γ-bromo-2-nitrobutyrophenone and γ-chloro-2-nitrobutyrophenone were obtained in good purity and high yield.

EXAMPLE 3

(A) A mixture of 2.9 g of γ-bromo-4-fluoro-2-nitrobutyrophenone, 1.25 g of ethylene glycol, 2.2 g of ethylene sulfite, 0.38 g of p-toluenesulfonic acid monohydrate and 20 ml of toluene was heated under refluxing for 9 hours. After cooling, the reaction mixture was diluted with 40 ml of 5% aqueous sodium hydroxide solution, and the toluene layer was separated. The aqueous layer was extracted with toluene, and the combined organic layer was washed with water, dried over anhydrous sodium sulfate and concentrated under reduced pressure to yield 3.1 g of 4-bromo-1-(4-fluoro-2-nitrophenyl)-1,1-ethylenedioxy-n-butane as an oil.

(B) A mixture of 117 g of γ-bromo-4-fluoro-2-nitrobutyrophenone, 50 g of ethylene glycol, 7.7 g of p-toluenesulfonic acid monohydrate and 500 ml of benzene was heated under refluxing for 60 hours, during which the water produced was eliminated as an azeotropic mixture by the use of the Dean-Starke's apparatus. After cooling, the reaction mixture was washed with water and diluted aqueous sodium bicarbonate solution, dried over anhydrous sodium sulfate and concentrated under reduced pressure to yield 135 g of 4-bromo-1-(4-fluoro-2-nitrophenyl)-1,1-ethylenedioxy-n-butane as an oil. B.P. 135°–140° C (at 0.17 mmHg).

(C) In the same manner as above, 4-bromo-1-(2-nitrophenyl)-1,1-ethylenedioxy-n-butane and 4-chloro-1-(2-nitrophenyl)-1,1-ethylenedioxy-n-butane were obtained.

EXAMPLE 4

(A) A mixture of 3.7 g of 4-bromo-1-(4-fluoro-2-nitrophenyl)-1,1-ethylenedioxy-n-butane, 2.5 g of 4-hydroxy-4-(3-trifluoromethylphenyl)piperidine, 1.4 g of anhydrous potassium carbonate, a catalytic amount of potassium iodide and 20 ml of methyl isobutyl ketone was heated at 80°–90° C for 2 hours. After cooling, the reaction mixture was diluted with 100 ml of water and extracted with ethyl acetate. The extracts were washed with water and aqueous saturated sodium chloride solution, dried over anhydrous sodium sulfate and concentrated under reduced pressure to yield 4-[4-hydroxy-4-(3-trifluoromethylphenyl)piperidino]-1-(4-fluoro-2-nitrophenyl)-1,1-ethylenedioxy-n-butane as a residual oil.

(B) The residual oil was dissolved in a mixture of 27.5 g of isopropanol and 27.5 g of 20% hydrochloric acid and heated under refluxing for 1 hour. After concentrating under reduced pressure, the precipitated solid was recrystallized from isopropanol to yield 2.8 g of γ-[4-hydroxy-4-(3-trifluoromethylphenyl)piperidino]-4-fluoro-2-nitrobutyrophenone hydrochloride as crystals. M.P. 209°–210.5° C. The second crop (0.5 g) was obtained from the mother liquor, M.P. 205°–209° C. Free base was obtained by the conventional procedure, M.P. 109°–112° C (from aqueous ethanol).

EXAMPLE 5

A mixture of 9.4 g of γ-bromo-4-fluoro-2-nitrobutyrophenone, 7.1 g of 4-hydroxy-4-(3-trifluoromethylphenyl)piperidine, 4.0 of potassium carbonate, a catalytic amount of potassium iodide and 60 ml of toluene was stirred at room temperature for 10 hours. The resulting mixture was diluted with water and extracted with toluene-ethyl acetate (1:1), and the organic layer was extracted with cold 30% hydrochloric acid. The hydrochloric acid layer was washed with toluene, made alkaline with 20% aqueous sodium hydroxide solution under cooling and extracted with ethyl acetate. The extracts were washed with water, dried over anhydrous sodium sulfate and concentrated to yield 6.4 g of γ-[4-hydroxy-4-(3-trifluoromethylphenyl)piperidino]-4-fluoro-2-nitrobutyrophenone as a residual oil, which was converted into its hydrochloride by a conventional manner. M.P. 200°–209° C.

EXAMPLE 6

(A) A mixture of 4-bromo-1-(4-fluoro-2-nitrophenyl)-1,1-ethylenedioxy-n-butane (3.3 g), 4-hydroxy-4-(3-trifluoromethylphenyl)piperidine (1.96 g), potassium carbonate (1.1 g), potassium iodide (20 mg) and methyl isobutyl ketone (25 g) was heated under refluxing for one hour. To the resulting mixture, 13% hydrochloric acid (8.2 g) was added under cooling, and the precipitated crystals were collected by filtration, washed with toluene and dried to give 3.9 g (91.1%) of 4-[4-hydroxy-4-(3-trifluoromethylphenyl)piperidino]-1-(4-fluoro-2-nitrophenyl)-1,1-ethylenedioxy-n-butane hydrochloride. M.P. 229° C (decomp.).

(B) A mixture of the ethylenedioxy compound obtained above (1.87 g), 15% hydrochloric acid (17.1 g) and ethanol (13 g) was heated under refluxing for 1 hour, concentrated under atmospheric pressure and cooled with an ice-salt bath for 1 hour. The precipitated crystals were collected by filtration to give 1.6 g (93%) of γ-[4-hydroxy-4-(3-trifluoromethylphenyl)piperidino]-4-fluoro-2-nitrobutyrophenone hydrochloride. M.P. 209° C.

EXAMPLE 7

In a similar manner to Example 4, 5 or 6, the following γ-(secondary amino)-o-nitrobutyrophenones were obtained by the use of a suitable secondary amine in place of 4-hydroxy-4,3-trifluoromethylphenylpiperidine:

γ-[4-(4-Chlorophenyl)-4-hydroxypiperidino]-4-fluoro-2-nitrobutyrophenone hydrochloride, M.P. 199.5°–202° C;

γ-[4-(4-Chloro-3-trifluoromethylphenyl)-4-hydroxypiperidino]-4-fluoro-2-nitrobutyrophenone, M.P. 144.5°–146.5° C; hydrochloride, M.P. 248° C (decomp.);

γ-[4-(3,4-Dichlorophenyl)-4-hydroxypiperidino]-4-fluoro-2-nitrobutyrophenone hydrochloride, M.P. 211.5°–212.5° C;

γ-[4-(3-Chloro-4-methylphenyl)-4-hydroxypiperidino]-4-fluoro-2-nitrobutyrophenone hydrochloride, M.P. 236.5° C (decomp.);

γ-(4-Phenylpiperidino)-4-fluoro-2-nitrobutyrophenone hydrochloride, M.P. 178°–188° C;

γ-(4-Oxo-1-phenyl-1,3,8-triazaspiro[4,5]decan-8 -yl)-4-fluoro-2-nitrobutyrophenone hydrochloride, M.P. 228°–229° C;

γ-[4-(2-Oxo-1-benzimidazolinyl)piperidino]-4-fluoro-2-nitrobutyrophenone, M.P. 138°–142° C;

γ-[4-(4-Chlorobenzyl)-4-hydroxypiperidino]-4-fluoro-2-nitrobutyrophenone hydrochloride, M.P. 210° C (decomp.);

γ-[4-(2-Methoxyphenyl)piperazino]-4-fluoro-2-nitrobutyrophenone hydrochloride, M.P. 206° C (decomp.);

γ-[4-Hydroxy-4-(4-methylphenyl)piperidine]-4-fluoro-2-nitrobutyrophenone, etc.

EXAMPLE 8

By substituting 4-bromo-1-(2-nitrophenyl)-1,1-ethylenedioxy-n-butane for 4-bromo-1-(4-fluoro-2-nitrophenyl)-1,1-ethylenedioxy-n-butane in Example 4, 5, 6 or 7, the following compounds were obtained:
γ-[4-Hydroxy-4-(3-trifluoromethylphenyl)piperidino]-2-nitrobutyrophenone;
γ-[4-(4-Chlorophenyl)-4-hydroxypiperidino]-2-nitrobutyrophenone;
γ-(4-Benzyl-4-hydroxypiperidino)-2-nitrobutrophenone;
γ-[4-(4-Chlorobenzyl)-4-hydroxypiperidino]-2-nitrobutyrophenone;
γ-[4-(4-Chloro-3-trifluoromethylphenyl)-4-hydroxypiperidino]-2-nitrobutyrophenone;
γ-(4-Oxo-1-phenyl-1,3,8-triazaspiro[4,5]decan-8-yl)-2-nitrobutyrophenone;
γ-[4-(2-Oxo-1-benzimidazolinyl)piperidino]-2-nitrobutyrophenone;
γ-[4-(2-Methoxyphenyl)piperazino]-2-nitrobutyrophenone, etc.

EXAMPLE 9

A mixture of 4.9 g of γ-[4-hydroxy-4-(3-trifluoromethylphenyl)piperidino]-4-fluoro-2-nitrobutyrophenone hydrochloride, 1.0 g of 5 % palladium on charcoal (50 % wet reagent) and 80 g of methanol was vigorously stirred in hydrogen atmosphere at room temperature until the theoretical amount of hydrogen was consumed. The catalyst was filtered off and washed with hot methanol, and the filtrate was concentrated under reduced pressure. The residual solid was triturated with isopropanol, collected by filtration and washed with diisopropyl ether to afford 3.9 g of γ-[4-hydroxy-4-(3-trifluoromethylphenyl)piperidino]-2-amino-4-fluorobutyrophenone monohydrochloride. M.P. 202°–204° C. The free base of this product was obtained by the conventional procedure. M.P. 106°–107° C (recrystallized from toluene).

EXAMPLE 10

A mixture of 4-[4-hydroxy-4-(3-trifluoromethylphenyl)piperidino]-1-(4-fluoro-2-nitrophenyl)-1,1-ethylenedioxy-n-butane (6.42 g), water (20 g), ethanol (80 g) and concentrated hydrochloric acid (1.4 g) was warmed to 70° C. Iron powder (6.7 g) was added portionwise to the mixture and gently refluxed for 1 hour. After the precipitate was filtered off and washed with hot ethanol, the filtrate was concentrated in vacuo. The residue was made alkaline with 10% aqueous sodium hydroxide solution and the whole was extracted with ethyl acetate. The extract was washed with water, dried over anhydrous sodium sulfate and evaporated under reduced pressure. The residue was dissolved in isopropanol (25 g), and concentrated hydrochloric acid (5 g) was added thereto under cooling. The precipitated crystals were collected by filtration, washed with toluene and dried to yield 4.4 g (80%) of γ-[4-hydroxy-4-(3-trifluoromethylphenyl)piperidino]-2-amino-4-fluorobutyrophenone monohydrochloride. M.P. 208.5°–209.5° C.

EXAMPLE 11

By substituting γ-[4-hydroxy-4-(3-trifluoromethylphenyl)piperidino]-4-fluoro-2-nitrobutyrophenone hydrochloride for 4-[4-hydroxy-4-(3-trifluoromethylphenyl)piperidino]-1-(4-fluoro-2-nitrophenyl)-1,1-ethylenedioxy-n-butane in Example 10, the same product was obtained.

EXAMPLE 12

In a similar manner to Example 9 or 10, the following o-aminobutyrophenone compounds were obtained:
γ-[4-(4-Chlorophenyl)-4-hydroxypiperidino]-2-amino-4-fluorobutyrophenone hydrochloride, M.P. 235° C (decomp.);
γ-[4-(4-Chloro-3-trifluoromethylphenyl)-4-hydroxypiperidino]-2-amino-4-fluorobutyrophenon, M.P. 166°–167° C;
γ-[4-(3,4-Dichlorophenyl)-4-hydroxypiperidino]-2-amino-4-fluorobutyrophenone hydrochloride, M.P. 214°–214.5° C;
γ-[4-(3-Chloro-4-methylphenyl)piperidino]-2-amino4-fluorobutyrophenone hydrochloride, M.P. 207°–210° C;
γ-(4-Phenylpiperidino)-2-amino-4-fluorobutyrophenone hydrochloride, M.P. about 185° C;
γ-(4-Oxo-1-phenyl-1,3,8-triazaspiro[4,5]decan-8-yl)-2-amino-4-fluorobutyrophenone, M.P. 198° C;
γ-[4-(2-Oxo-1-benzimidazolinyl)piperidino]-2-amino-4-fluorobutyrophenone, M.P. 230°–235° C;
γ-[4-(4-Chlorobenzyl)-4-hydroxypiperidino]-2-amino-4-fluorobutyrophenone hydrochloride, M.P. 155° C (decomp.);
γ-[4-(2-Methoxyphenyl)piperazino]-2-amino-4-fluorobutyrophenone, M.P. 83°–87° C;
γ-[4-Hydroxy-4-(4-methylphenyl)piperidino]-2-amino-4-fluorobutyrophenone, M.P. 140° C;
γ-(4-Benzyl-4-hydroxypiperidino)-2-aminobutyrophenone, M.P. 123° C;
γ-[4-(4-Chlorobenzyl)-4-hydroxypiperidino]-2-aminobutyrophenone, M.P. 138° C;
γ-(4-Oxo-1-phenyl-1,3,8-triazaspiro[4,5]decan-8-yl)-2-aminobutyrophenone, M.P. 180° C, etc.

What is claimed is:
1. A compound of the formula:

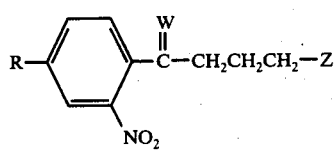

wherein R is a hydrogen atom or a fluorine atom, W is an oxygen atom, an ethylendiozy group or an ethylenedithio group and Z is a secondary amino group of the formula:

wherein Ar is an unsubstituted phenyl group or a phenyl group substituted with one or two substituents selected from the group consisting of halogen, methyl, methoxy and trifluoromethyl and $R_1$ is a hydrogen atom or a hydroxyl group, or a pharmaceutically acceptable acid addition salt thereof.

2. The compound according to claim 1, wherein W is an oxygen atom.

3. The compound according to claim 2, wherein R is a fluorine atom.

4. The compound according to claim 1, which is selected from the group consisting of γ-[4-hydroxy-4-(3-trifluoromethylphenyl)piperidino]-4-fluoro-2-nitrobutyrophenone, γ-[4-(4-chlorophenyl)-4-hydroxypiperidino]-4-fluoro-2-nitrobutyrophenone, γ-[4-(4-chloro-3-trifluoromethylphenyl)-4-hydroxypiperidino]-4-fluoro-2-nitrobutyrophenone, γ-[4-(3,4-dichlorophenyl)-4-hydroxypiperidino]-4-fluoro-2-niteobutyrophenone, γ-[4-(3-chloro-4-methylphenyl)-4-hydroxypiperidino]-4-fluro-2-nitrobutyrophenone, γ-[4-(4-chlorobenzyl)-4-hydroxypiperidino]-4-fluoro-2-nitrobutyrophenone, γ-[4-hydroxy-4-(4-methylphenyl)-piperidino]-4-fluoro-2-nitrobutyrophenone, γ-[4-hydroxy-4-(3-trifluoromethylphenyl)-piperidino]-2-nitrobutyrophenone, γ-[4-(4-chlorophenyl)-4-hydroxypiperidino]-2-nitrobutyrophenone, γ-[4-(4-chlorobenzyl)-4-hydroxypiperidino]-2-nitrobutyrophenone, and γ-[4-(4-chloro-3-trifluoromethylphenyl)-4-hydroxypiperidino]-2-nitrobutyrophenone.

5. A central nervous system depressant composition which comprises as the active ingredient at least one of the γ-(secondary amino)-orthonitrobutyrophenones of the formula:

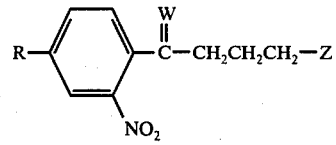

wherein R is a hydrogen atom or a fluorine atom, W is an oxygen atom, an ethylenedioxy group or an ethylenedithio group, and Z is a secondary amino group of the formula:

wherein Ar is an unsubstituted phenyl group or a phenyl group substituted with one or two substituents selected from the group consisting of halogen, methyl, methoxy and trifluoromethyl and $R_1$ is a hydrogen atom or a hydroxyl group, or a pharmaceutically acceptable acid addition salt thereof, and at least one pharmaceutically acceptable carrier or diluent.

6. A method for preparation of the pharmaceutical composition according to claim 5, which comprises admixing the active ingredient with at least one pharmaceutically acceptable carrier or diluent.

7. The compound γ-[4-hydroxy-4-(3-trifluoromethylphenyl)piperidino]-4-fluoro-2-nitrobutyrophenone.

8. A method for depressing the central nervous system which comprises administering to a patient in need of such treatment an effective depressant amount of the composition of claim 5.

* * * * *